US011593764B2

United States Patent
Ranieri et al.

(10) Patent No.: US 11,593,764 B2
(45) Date of Patent: Feb. 28, 2023

(54) REMOTE MEDICATION DELIVERY SYSTEMS

(71) Applicant: Data Vault Holdings, Inc., New York, NY (US)

(72) Inventors: Daniel Ranieri, Tucson, AZ (US); David Bradley, Tucson, AZ (US)

(73) Assignee: DATA VAULT HOLDINGS, INC., New York, NY (US)

( * ) Notice: Subject to any disclaimer, the term of this patent is extended or adjusted under 35 U.S.C. 154(b) by 384 days.

(21) Appl. No.: 14/979,742

(22) Filed: Dec. 28, 2015

(65) Prior Publication Data

US 2017/0185734 A1 Jun. 29, 2017

(51) Int. Cl.
| G06Q 10/10 | (2012.01) |
| G06Q 10/109 | (2023.01) |
| H04L 9/40 | (2022.01) |
| G16H 20/10 | (2018.01) |
| G16H 40/67 | (2018.01) |

(52) U.S. Cl.
CPC ......... *G06Q 10/109* (2013.01); *G16H 20/10* (2018.01); *G16H 40/67* (2018.01); *H04L 63/0861* (2013.01)

(58) Field of Classification Search
CPC ............... G06F 19/3418; G16H 20/10; G06Q 50/22–24
See application file for complete search history.

(56) References Cited

U.S. PATENT DOCUMENTS

| 4,237,344 | A | 12/1980 | Moore |
| 5,377,258 | A | 12/1994 | Bro |
| 6,173,212 | B1* | 1/2001 | Valerino, Sr. .......... B65G 51/34 700/218 |
| 6,898,299 | B1* | 5/2005 | Brooks .................... G07C 9/37 382/115 |
| 2001/0049321 | A1 | 12/2001 | Cohen et al. |
| 2002/0045519 | A1 | 4/2002 | Watterson |
| 2002/0048600 | A1* | 4/2002 | Bhatt ................... A61K 9/0004 424/465 |
| 2002/0082142 | A1 | 6/2002 | Cannon et al. |
| 2003/0004758 | A1 | 1/2003 | Luttrell |
| 2004/0030581 | A1* | 2/2004 | Leven .................... G16H 40/67 705/2 |
| 2004/0162702 | A1 | 8/2004 | Pandipati et al. |
| 2007/0201727 | A1 | 8/2007 | Birrell et al. |
| 2007/0232450 | A1 | 10/2007 | Hanoun |
| 2008/0207335 | A1* | 8/2008 | DiMichele ............. G07F 17/32 463/46 |
| 2008/0215627 | A1* | 9/2008 | Higgins ................ G06Q 10/06 |
| 2009/0048872 | A1 | 2/2009 | Toy et al. |
| 2009/0197739 | A1 | 8/2009 | Hashimoto |

(Continued)

FOREIGN PATENT DOCUMENTS

| CN | 107316222 A | * | 11/2017 | ............ G06Q 30/06 |
| WO | 2012156374 A1 | | 11/2012 | |

*Primary Examiner* — John A Pauls

(74) *Attorney, Agent, or Firm* — Goodhue, Coleman & Owens, P.C.

(57) ABSTRACT

A system and method for medication delivery. Information is received indicating a user is scheduled to receive medication. A route between a dispensary storing the medication and a location of the user is determined. The medication is sent in a container from the dispensary to the location utilizing the route.

20 Claims, 5 Drawing Sheets

(56) References Cited

U.S. PATENT DOCUMENTS

| | | | | |
|---|---|---|---|---|
| 2009/0326339 | A1* | 12/2009 | Horvitz | G06Q 10/00 600/301 |
| 2010/0013597 | A1* | 1/2010 | Determan | G07C 9/00563 340/5.82 |
| 2010/0079046 | A1* | 4/2010 | Vint | A47B 88/46 312/333 |
| 2010/0100226 | A1* | 4/2010 | Valerino, Sr. | G06Q 10/00 700/215 |
| 2010/0120585 | A1 | 5/2010 | Quy | |
| 2011/0092825 | A1* | 4/2011 | Gopinathan | G06Q 40/08 600/483 |
| 2011/0267459 | A1 | 11/2011 | Choi | |
| 2011/0295613 | A1 | 12/2011 | Coyne | |
| 2012/0209421 | A1* | 8/2012 | Valerino, Sr. | G06Q 10/00 700/225 |
| 2012/0296455 | A1 | 11/2012 | Ohnemus et al. | |
| 2013/0129217 | A1 | 5/2013 | Gupta | |
| 2013/0151267 | A1* | 6/2013 | Mehdizadeh | G06Q 50/22 705/2 |
| 2013/0196822 | A1 | 8/2013 | Watterson et al. | |
| 2013/0267385 | A1 | 10/2013 | Watterson et al. | |
| 2014/0046690 | A1* | 2/2014 | Gunderson | G16H 10/20 705/3 |
| 2014/0352580 | A1* | 12/2014 | Stradiota | G07C 9/37 109/23 |
| 2014/0375470 | A1* | 12/2014 | Malveaux | G16H 20/30 340/870.01 |
| 2015/0048102 | A1* | 2/2015 | Dickie | A61J 1/03 221/2 |
| 2015/0120094 | A1* | 4/2015 | Kimchi | G05D 1/00 701/3 |
| 2015/0335950 | A1 | 11/2015 | Eder | |
| 2016/0140496 | A1* | 5/2016 | Simms | B64C 39/024 705/337 |
| 2016/0159496 | A1* | 6/2016 | O'Toole | B64C 39/024 244/110 E |
| 2016/0162660 | A1* | 6/2016 | Strong | A61J 7/0076 700/236 |
| 2016/0185466 | A1* | 6/2016 | Dreano, Jr. | G06Q 10/083 705/26.81 |
| 2016/0257426 | A1* | 9/2016 | Mozer | B64F 1/362 |
| 2016/0321847 | A1* | 11/2016 | Briskey | G07C 9/00571 |
| 2016/0361032 | A1 | 12/2016 | Carter | |
| 2016/0378921 | A1 | 12/2016 | Ohnemus et al. | |
| 2017/0010665 | A1* | 1/2017 | Tanaka | H04L 63/0869 |
| 2017/0132393 | A1* | 5/2017 | Natarajan | G06Q 10/087 |
| 2017/0304679 | A1 | 10/2017 | Orfield | |

* cited by examiner

REMOTE MEDICATION DELIVERY SYSTEMS

BACKGROUND

In recent years, life expectancy rates have improved dramatically around the world. The ability to live longer has increased significantly because of better health care, available information, medication, exercising routines, medical devices, and so forth. Many individuals seek to live independently as long as possible to the extent their health, mental state, and personal conditions allow. In many cases, individuals that live independently have been found to be happier and experience more fulfilled lives. Living independently as possible may be difficult for some individuals because of medication requirements, physical limitations, and other conditions for which they may need at least minimal assistance.

SUMMARY

One embodiment provides a system, method, device, and computer program product for medication delivery. Information is received indicating a user is scheduled to receive medication. A route between a dispensary storing the medication and a location of the user is determined. The medication is sent in a container from the dispensary to the location utilizing the route. The method may also be performed by a device including a processor a memory and a set of instructions executed to perform the described method. The method may also be executed as machine readable media.

Yet another embodiment provides a system for delivering medication. The system may include a pneumatic delivery system connected between one or more residences and a dispensary storing a plurality of medications. A computing system to receive information indicating a user is scheduled to receive medication, determine a route through the pneumatic delivery system between the dispensary and one of the one or more residences associated with the user.

BRIEF DESCRIPTION OF THE DRAWINGS

The present embodiments may be better understood, and numerous objects, features, and advantages made apparent to those skilled in the art by referencing the accompanying drawings.

DESCRIPTION OF EMBODIMENT(S)

Figure 1:
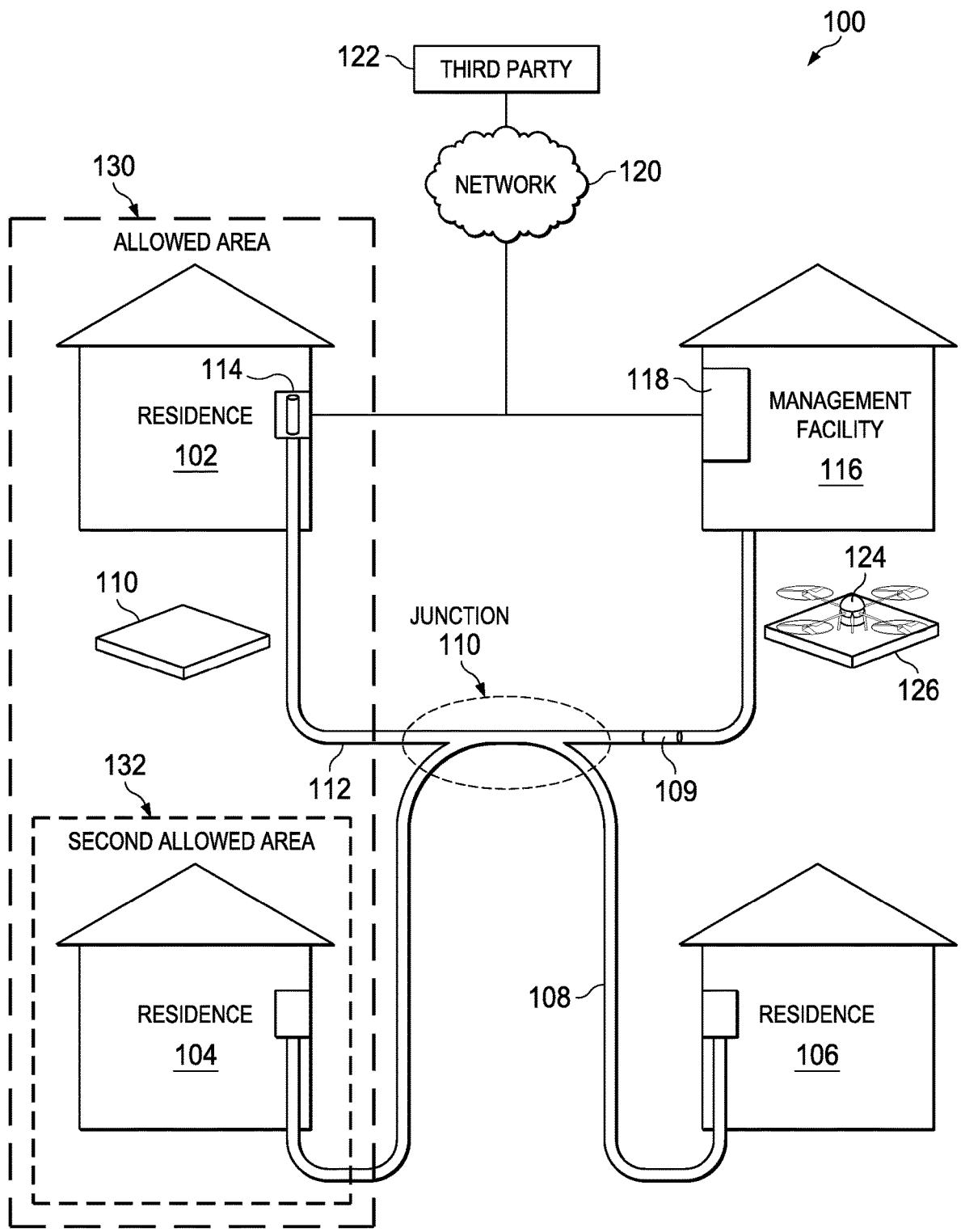
FIG. 1 is pictorial representation of a delivery and medication system in accordance with an illustrative embodiment.

The description that follows includes exemplary systems, methods, devices, techniques, instruction sequences and computer program products that embody techniques of the present inventive subject matter. However, it is understood that the described embodiments may be practiced without these specific details. In other instances, well-known instruction instances, protocols, structures, components, and techniques have not been shown in detail in order not to obfuscate the description.

The illustrative embodiments provide a distribution and monitoring system, method, and devices. A user as referred to herein may refer to a patient, resident of a facility, or other individual. A residence as referred to herein may refer to a home, apartment, assisted living facility, medical facility, commercial facility, or other location in which the user may permanently or temporarily reside or be located.

In one embodiment, the distribution system is utilized to distribute medication to one or more users. The medication may be delivered utilizing a predetermined schedule, in real-time, or based on a need or other manual selection. For example, the distribution system may be part of an assisted living facility that delivers medication for individual users or residents at meals based on their individual medical needs. The medications may include one or more different types, dosages, categories, or delivery types. The various embodiments may also provide tracking and verification information to ensure that the user received and/or utilized the medication. The facility may be a single facility or building or may be a distributed facility for delivering the medication.

The systems may include scanning equipment, monitoring devices, sensor, and other systems for determining the status of the user. For example, a wearable glucose monitor may be utilized to determine whether insulin or other medications are required for a diabetic user. Likewise, cameras, infrared scanners, or so forth, may be utilized to determine the location, pulse, and physical orientation of the user to determine whether medication or medical assistance are required. Integrated sensors may be configured to detect particular odors. For example, rotting food, mold, bodily fluids or waste, or other smells indicative of a potential problem may be sensed and reported. Thresholds may be utilized for the sensing equipment to ensure that alerts or reporting are not performed unnecessarily. As a result, medications may be delivered as needed. Real-time medication delivery may allow users to have improved circumstances and health.

In one embodiment, the medication is distributed from a central facility, such as a dispensary, pharmacy, administration office, or so forth. The distribution system may be automatic, or may be configured to interact with one or more administrators or medical professionals. In some embodiments, a central facility may serve multiple users to ensure that their medical and monitoring needs are met. In another embodiment, the administrator/caregiver and the user may have a one-to-one relationship. The medications and other items are distributed in accordance with country, state, county, and local laws and regulations for medication, medication delivery, and medical practitioners (e.g., doctors, pharmacists, nurse practitioners, etc.).

The medications may be delivered utilizing any number of delivery methods. In one embodiment, the delivery system includes a pneumatic tube network that is utilized to pneumatically drive containers to a location of the user for delivering medication. In another embodiment, one or more drones (flying or land based) may be utilized to deliver the medications. The delivery system may include a receiving point, dock, or other location configured to receive the medication associated with a user. In one embodiment, a lockbox is configured to receive containers that store the medication. The lockbox and the containers may individually or collectively include authentication systems for ensuring that the user receives the medication rather than another individual or party. For example, passwords, pins, biometrics (e.g., voice recognition, DNA, fingerprints, eye scans, etc.), may be utilized to authenticate the user.

As previously noted, monitoring equipment within the location, facility, or residence of the user may be utilized to perform monitoring. Monitoring may be performed by a medical professional, administrator, authorized observer, or family member or friend that is granted access.

FIG. 1 is pictorial representation of a delivery and medication system 100 in accordance with an illustrative embodiment. In one embodiment, the system 100 may include residences 102, 104, 106, a pneumatic system 108, a junction 110, a path 112, a lock box 114, a management facility 116, a computing system 118, a network 120, a third party 122, a drone 124, landing pads 126, 128, and allowed areas 130, 132.

The system 100 may represent any number of residences, facilities, or locations in which one or more users may reside or spend a significant amount of time whether permanently or temporarily. The management facility 116 is a location within which an administrator works, lives, or is temporarily located. For example, an administrator within the management facility 116 may serve multiple users within the residences 102, 104, 106. Users within the residences 102, 104, 106, may live there alone, as family unit, with a caregiver, or in other cases as circumstances require.

In one embodiment, the management facility 116 manages the care of the residences 102, 104, 106, including, for example, building maintenance, medication delivery, and status monitoring of the users. The computing system 118 may be utilized to automatically, semi automatically, or manually control the components of the system 100. For example, the computing system 118 may receive multiple feeds, sensor inputs, data, or other information for each of the residences 102, 104, and 106 as is further shown and FIG. 3. The computing system 118 may include one or more servers, databases, routers, switches, personal computers, mobiles devices, intelligent network devices, or so forth.

In one embodiment, the computing system 118 communicates with the other portions of the system 100 through the network 120. The communications within the delivery and medication system 100 may occur on any number of networks which may include wireless networks, data or packet networks, cable networks, satellite networks, private networks, alternative networks, and publicly switched telephone networks (PSTN). The network 120 represents the different types of communication network types and configurations. In particular, the network 120 may be utilized by the different portions of the system 100 to communicate with one or more cloud, social, or medical networks or software systems. The features of the illustrative embodiments may be implemented by one or more elements of the delivery and medication system 100 independently or as a networked implementation.

The communications environment 100 may further include any number of hardware and software elements that may not be shown in the example of FIG. 1. For example, the communications environment 100 may include fiber optic cables, coaxial cables, twisted pair wires, exchanges, switches, antennas, towers, switching centers, routers, application servers, media servers, media converters, service brokers, call agents, edge routers, gateways (signaling, trunking, access, sub, etc.), IP network service providers, adapters, exchanges, switches, users, and networks.

In one embodiment, the computing system 118 may include a specialized program, algorithm, or set of instructions that are executed by one or more processors to implement the systems and methods herein described. For example, the computing system 118 may act as a controller for the other portions of the system 100.

In one embodiment, the residences 102, 104, 106 are connected by the pneumatic system 108. The pneumatic system may also be referred to as a pneumatic tube transport (PTT) for moving cylindrical or round containers through a network of tubes by compressed air or by partial vacuum. The pneumatic system 108 may move one or more containers 109 through the pneumatic system 108 individually, concurrently, or simultaneously. In one embodiment, the pneumatic system 108 represents a number of tubes formed from plastic, glass, metal, wood, polymers, or so forth. The tubes of the pneumatic system 108 may take any number of shapes or paths, such as direct, free form, or grid-like.

The container 109 is configured to be communicated or move from the management facility 116 to any of the residences 102, 104, 106. The container 109 may be formed of a low resistance material or include bearings, wheels, or slides to encourage free motion within the pneumatic system 108. The pneumatic system 108 may include one or more junctions, such as junction 110. The junction 110 may be controlled by the computing system 118 to route the container 109 within the pneumatic system 108. For example, the junction 110 may include any number of actuators, ramps, doors, diverters, arms, or so forth that select one of the pathways of the pneumatic system 108 for routing the container 109. In one embodiment, the pneumatic system 108 includes smart connections, such as a connected network controller for each segment of the pneumatic system or for the junction 110 for controlling and tracking motion of the container 109 within the pneumatic system 108. For example, one or more buses or wires may be integrated with or connected to the tubes of the pneumatic system 108 to control components, such as the junction 110. The container 109 may be driven within the pneumatic system 108 utilizing compressed gases and/or suction generated by one or more pumps integrated with or connected to the system. Sensor within the pneumatic system 108 may also be utilized to detect the location of the container 109 and to control various components, such as the junction 110.

The pneumatic system 108 may have separate tube paths that terminate at each of the residences 102, 104, 106 and management facility 116. In one embodiment, the various tubes in of the pneumatic system 108 may terminate at a lockbox, such as the lockbox 114. Each of the residences 102, 104, 106, and the management facility 116 may include a lockbox 114, dock, or so forth. The lockbox 114 may be utilized to securely receive the container 109. For example, the lockbox 114 may be configured to receive one or more containers simultaneously, and to store the containers for delivery at the specified time. The lockbox 114 may include one or more locking mechanisms that are interconnected with an authentication system. The lockbox 114 may receive an identifier or authentication information to ensure that the medication is delivered to the user for consumption (and not to another party that may live at the applicable residence or that may be visiting). For example, a passcode, pin, voice identifier, or biometric identification may be utilized to release medication within the lockbox 114 and container 109 to the user. In another example, an administrator in the management facility 116 may send a command to the lockbox 114 to release the container 109 and/or medication to the user based on audible, visual, or other authentication.

In another embodiment, one or more of the residences 102, 104, 106 may include the landing pad 126. The landing pads 126, 128 are configured to receive the drone 124. For example, medications may be loaded onto the container 109 that is then attached to the drone 124. The drone 124 may then fly or drive to the landing pad 128 from the landing pad 126. In one embodiment, the drone 124 may travel to the location of the landing pad 128 and deliver the container 109, after which the drone returns back to the landing pad or 126 to be loaded, charged, maintained, or prepared for the next delivery. For example, the drone 124 may be preprogrammed with a route to reach the pad 110 of the residence 102. In another embodiment, the drone 124 may remain at the residence 102 until the container 109 is retrieved from the drone 124 or until subsequently needed. The drone 124 may leave the container 109 on the landing pad 128. The drone 124 may alternatively dock with the lockbox 114 to deliver the medication for the user of the residence 102. The medications may be delivered in a stand-alone form that is easily consumed, injected, or otherwise applied or within a small container as is herein described.

In one embodiment, the route or delivery path, including speed, direction, altitude, and distance between the landing pad 126 and the landing that 128 may be pre-programmed or loaded into the drone 124 or wirelessly communicated from the computing device 118 to the drone 124. In another embodiment, the landing pad 126, 128, lockbox 114, or the residence 102 may include a signal or beacon that is utilized to signal a location to the drone 124. The drone 124 may include one or more camera systems, sensors, or so forth for navigating the residences 102, 104, 106, the, power lines, trees, or other obstacles within the environment represented by the system 100. As a result, the drone 124 may determine a travel path in real-time. In one embodiment, the landing pad 126 may be retracted from the management facility 116 (or the residences 102, 104, 106) in order to allow an administrator or user to prepare the drone 124 and the corresponding container 109. In addition, the drone 124 may be accessed from within the residence 102 utilizing a retractable pad regardless of the weather or other conditions. In another embodiment, the drone 124 may be configured to utilize pre-programmed flight or drive information as well as real-time sensing to avoid new or temporary obstacles (e.g., delivery trucks, power lines, birds, people, etc.). The computing system 118 may communicate the routes to the drone 124 utilizing a wired or wireless connection for storage in the memory or navigation system of the drone 124. In another embodiment, a robotic system or kiosk of the management facility 116 may be utilized to load and unload the medicine or other payload carried by the drone 124.

In one embodiment, the system 100 may also be configured to track users. The tracking may be performed based on their own consent, consent of a guardian/custodian, court order, or so forth. In one embodiment, the allowed area 130 is a range, perimeter, or area associated with the residence 102 and the corresponding user. For example, the allowed area 130 may specify areas that the user is allowed to be while areas outside the allowed area 130 may be disallowed. The user may wear a location device (e.g., GPS tracker, Apple watch, Android wear, smart jewelry or clothing, etc.) that indicates the location and physical orientation of the user at any time. In another embodiment, a number of cameras within the system 100 may be utilized to determine the location of the user without violating the user's privacy As a result, the user may be able to move anywhere within the allowed area 130 without an alert or alarm being generated. If the user associated with the residence 102 is outside the allowed area 130, an alert or alarm may be generated. The alarm may be generated for an administrator within the management facility 116. In another embodiment, the alert is for a third party, such as a friend or family member of the user. Any number of criteria, user preferences, or parameters may be utilized to determine who, how, and when alerts or alarms are generated.

In one embodiment, the allowed area 130 may be dynamically reconfigured based on privileges, time of day, days of the week, or so forth. For example, the allowed area 130 may be automatically expanded to cover a recreation area near the management facility 118 based on a request from a user or on specified days. The user may make requests through one or more applications or programs available to the user that are tracked by the system 100. The allowed area 130 may also be beneficial for users that are experiencing memory issues. For example, an alert may be given to the user prompting him to return to the allowed area 130. In one embodiment, the alert is given through a smart devices, such as cell phone, anklet, necklace, smart watch (e.g., Apple watch, Samsung watch, speaker, etc.), or other smart wearable product issued to the user.

As shown, the second allowed area 132 may be associated with a user of the residence 104. The size, shape, and other information associated with the allowed area 130, 132 may vary based on the individual circumstances of the users of the residences 102, 104. For example, the allowed area 130 may include both the residence 102 and the residence 104. However, the allowed area 132 may only include the residence 104.

Figure 2:
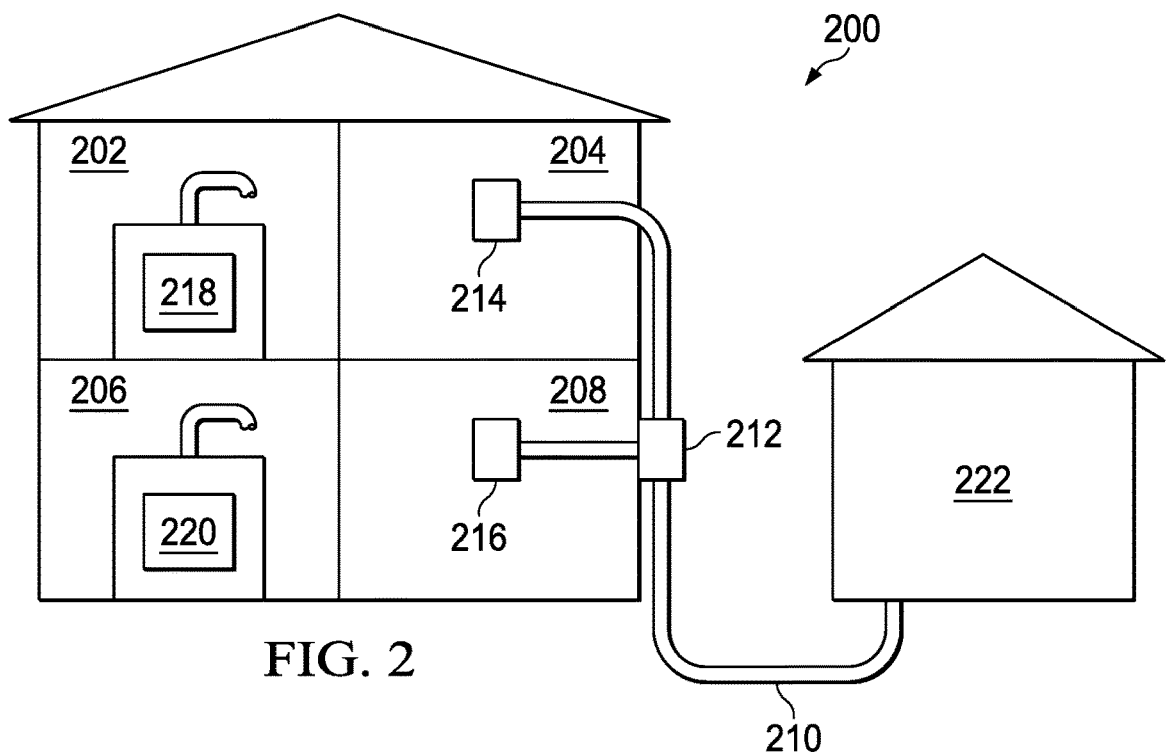
FIG. 2 is a pictorial representation of another delivery and medication system in accordance with an illustrative embodiment.

FIG. 2 is a pictorial representation of another delivery system 200 in accordance with an illustrative embodiment. In one embodiment, the system 200 may include a facility 201, residences 202, 204, 206, 208, a pneumatic system 210, a junction 212, lockboxes 214, 216,218, 220, and a dispensary 222. As shown, all or portions of the system 200 represent or may be integrated with the system 100 of FIG. 1.

As shown, the delivery system 200 may be utilized for single occupancy residences, multiple occupancy residences, and so forth. In one embodiment, the facility 201 may be a multi-level residence facility. For example, individual users or groups of users may live in each residence 202, 204, 206, 208. As shown, the residences 202 and 206 include a first type of lock box 218, 220 and the residences 204, 208 include a second type of lockbox 214, 216.

As previously described, the lockboxes 214, 216 are interconnected with the pneumatic system 210. The lockboxes 214 and 216 receive one or more containers through the pneumatic system 210. As previously noted, the junction 212 routes the containers to the lockboxes 214, 216, respectively. In another embodiment, the pneumatic system 210 may also be interconnected to the lockboxes 218, 220.

As shown, the lockboxes 218, 220 may be integrated with furniture or a fixture, such as a kitchen sink, desk, drawers, or cabinets. The lockboxes 218, 220 may be stocked by a delivery person or device. The delivery person may access the lockboxes 218, 220 from inside the residence 202, 206, or from the outside thereof. For example, the lockboxes 218, 220 may have an access door or port that is available from a hallway, secured room, garage, exterior wall, or other location for the delivery person to access the lockboxes 218, 222 to deliver medications, or other sensitive items. For example, the lockboxes 218, 220 may be utilized to deliver sensitive documents or authorization information for the users. The lockboxes 218, 220 allow the user to more easily access the medications. The lockboxes 218 are secure containers. The lockboxes 218, 220 may include one or more doors for access by both a delivery person and a user. For example, a key lock on a first door of the lock box 218 may open into a utility closet for access by a delivery person and a biometric lock (e.g., fingerprint, voice, etc.) on a second door of the lock box 218 may open into the residence 202 for access by a user as needed. The lockboxes 218, 220 may include the secured doors (and hinges) and may be sealed against outside influences (e.g., moisture, fire, poor air conditioning, heat, etc.).

In one embodiment, the lockboxes 214, 216, 218, 220 are voice controlled. For example, the user may request "Please give me my medicine." Once the user's voice is recognized or another authentication is verified, one or more of the lockboxes, 214, 216, 218, 220 may open to deliver the medication or other secured item. As previously disclosed, a pin, passcode, fingerprint or other information may also be utilized. In one embodiment, a radio frequency identifier (RFID) chip, near field communication (NFC) transceiver, or other similar component carried by, worn, or injected in the user may be utilized to authenticate the user.

Figure 3:
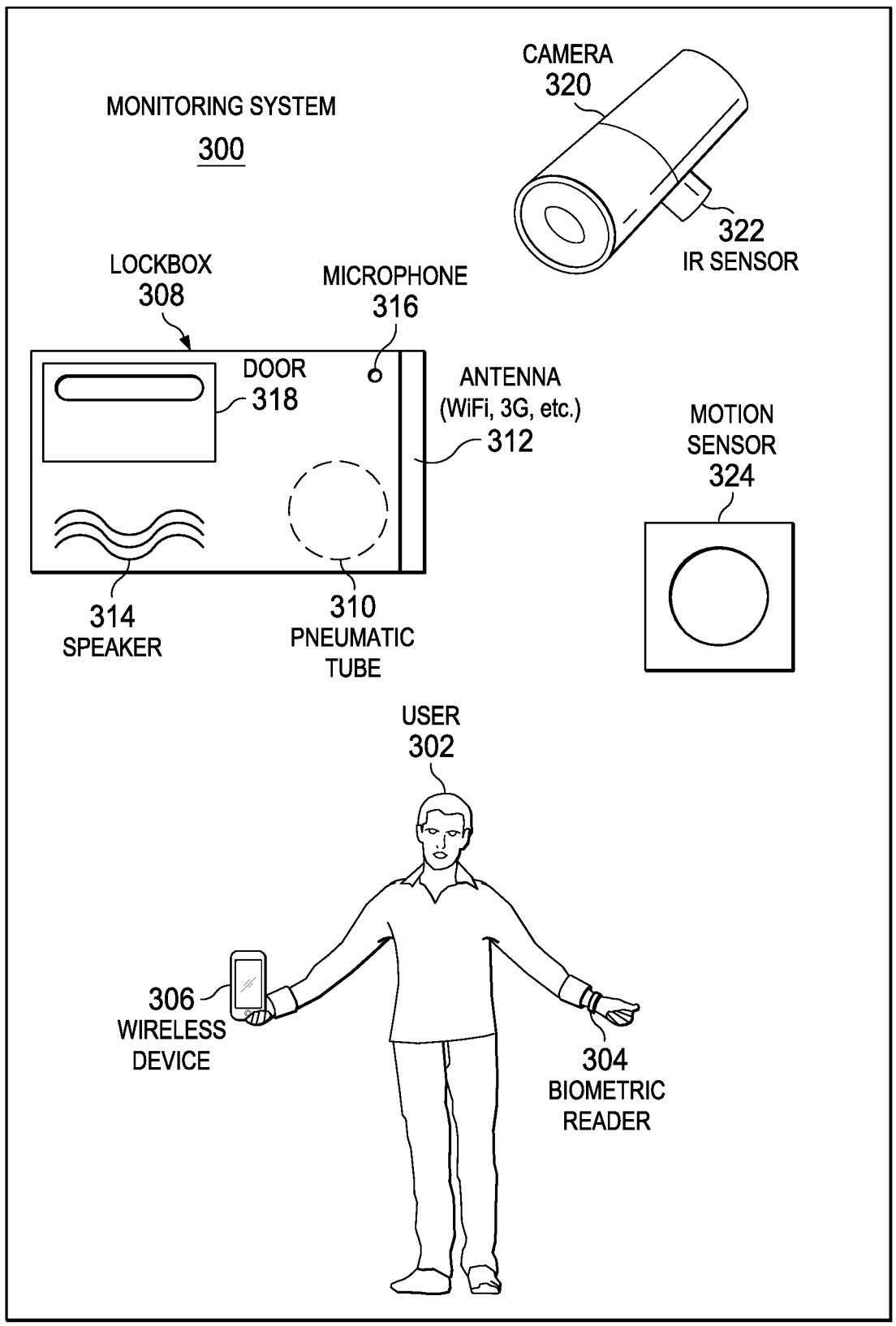
FIG. 3 is a pictorial representation of a monitoring system in accordance with an illustrative embodiment.

FIG. 3 is a pictorial representation of a monitoring system 300 in accordance with an illustrative embodiment. The monitoring system 300 may include any number of devices or components as illustrated in the systems 100 and 200 of FIGS. 1 and 2. In one embodiment, the monitoring system 300 may include a user 302, a biometric reader 304, a wireless device 306, a lockbox 308, a pneumatic tube 310, an antenna 312, a speaker 314, a microphone 316, a door 318, a camera 320 an infrared (IR) scanner 322, and a motion sensor 324.

In one embodiment, the lockbox 308 may be electrically powered. For example, the lockbox 308 may be connected to the wiring of the residence. In another embodiment, the lockbox 308 may include batteries for powering the lockbox 308 as a stand-alone device. The batteries may power the lockbox 308 even when there are power outages, intermittent power, or other potential issues. The door 318 is configured to open the lockbox 308 to access one or more containers, medications, or other items within. In one embodiment, the door 318 may only be opened by entering a combination, code, password, a number, biometric, or so forth. As a result, the lockbox 308 may include one or more keyboards, combinations, or so forth. In another embodiment, the lockbox 308 may include another door or port (not shown) on the backside or side of the lockbox 308 for another party to access or fill the lockbox 308 as is described herein.

In one embodiment, the lockbox 308 alerts the user 302 when a container has been delivered to the lockbox 308. The lockbox 308 may include any number of indicators, such as LEDs, touchscreens, or so forth, that display information, data, or alerts to the user 302. For example, the indicators may indicate when the lockbox 308 is full or has received content, when empty, or other potential issues. The door 318 may also include a window or peephole (not shown) for the user to determine whether one or more containers are within the lockbox 308. The window may be utilized to determine whether the container needs to be retrieved or returned to the dispensary.

The speaker 314 may be configured to play audio information to the user 302. For example, through the speaker 314, the user 302 may receive instructions to remove the container within the lockbox 308 and to take the associated medication. The speaker 314 may also be utilized to provide instructions for taking the medication, such as "Please take this medication after eating a full meal and with a half glass of water." Instructions may be provided for other types of medicines, topical, injection, or so forth. The speaker 314 may be controlled through logic of the lockbox 308 controlling the operations thereof.

The microphone 316 may be utilized to receive important feedback from the user 302. For example, the user 302 may ask for assistance. In another embodiment, the user may request instructions regarding how to open the lockbox 308 or take a particular medication. The lockbox 308 may also act as an emergency beacon. For example, if the user 302 is injured or otherwise needs assistance, the user 302 may provide a request for help, keyword, or other information to receive help from either an administrator, paramedics, or other response personnel. As a result, the lockbox 308 may act as a lifeline for the user 302. The lockbox 308 may also function as an emergency router to receive alerts from a local device within the residence or location before relaying the message, communication, or alert to a central system, caretaker, administrator, number of users, or so forth. For example, an application executed by the wireless device 306 (e.g., a cell phone or wearable utilized by the user 302) may prompt the user 302 for his/her status and in response to a non-response or response indicating that there is a problem may take additional actions, such as activating the camera 324 or other sensors of the monitoring system 300. Any number of other speakers, microphones, and sensors within the system 300 may be utilized to determine relevant information, communicate with the user 302, and receive meaningful feedback. The microphone 316 may also be utilized to perform voice recognition or receive a password before the door 310 is unlocked for access by the user 302. For example, the user may be required to state his name and a pass phrase to open the door 308.

The antenna 312 may be configured to communicate with any number of other smart devices within the system 300 or environment. In one embodiment, the lockbox 308 may communicate with a computing device that controls a number of lockboxes from an administrator facility. The antenna 312 may be connected to a wireless network interface that communicates with a processor, chipset, or logic of the lockbox 308. The lockbox 308 may be connected to a hardwired communications connection or line or may utilize a wireless connection, such as Wi-Fi, cellular data, or so forth.

Lockbox 308 may be configured to communicate with one or more computing or communications devices within the residence. For example, the antenna 312 may communicate with the wireless device 306. Alerts regarding deliveries, scheduled medicine consumption, status verification, or so forth, may be sent to the wireless device 306. Likewise, the lockbox 308 may receive user input, feedback, and so forth through the wireless device 306. Additional relevant information may be communicated from the lockbox 308 to the wireless device 306. The lockbox 308 may also communicate with cellular towers and systems or remote devices, such as computer systems utilized by administrators assigned to the user 302.

Various devices within the system 300 may be configured to determine the location, orientation, and status of the user 302. In one embodiment, the location of the user 302 may be determined utilizing one or more cameras, such as the camera 320 that may be installed throughout the residence. The camera 320 may be configured to sense any number of spectrums for determining distinct information about the location and condition of the user (e.g., hyperspectral imaging, thermal, infrared, X-ray, etc.). The camera 320 may also include an electronic nose for detecting odors or flavors. The example, the camera 320 may include any number of chemosensors or gas chromatography devices for detecting odors. The odor sensing devices may include a sampling unit, sensor array, pattern recognition modules, and a computing/logic system. For example, the camera 320 may be configured to detect a number of distinct smells, such as mold, rotten food, excessive bodily waste or fluids, or so forth. These types of smells may indicate that there is a problem within the monitoring system 300 (e.g., residence, room, etc.) or that the user 302 may need assistance with various issues. For example, if the user 302 is in the first stages of Alzheimer's disease, the user 302 may still be functional enough to take care of himself, but may forget to wash the dishes which may detected by the camera 320 as a putrid odor that may communicate an alert that a caregiver needs to provide a reminder, some instructions, or assistance to the user 302 audibly through the speaker 314, visually through a connected display (e.g., wireless device, television, computer, heads up display, etc.) or in person.

The monitoring system 300 may also include one or more motion sensors 324 to determine the location of the user 302, an activity level of the user, 302 and other information associated with the user 302. This information may be saved to a database accessible to a caregiver, administrator, or the user 302. The biometric reader 304 may also be utilized to determine the location of the user 302 utilizing wireless triangulation, radio frequency imaging, signal differential, global positioning, or so forth. In one embodiment, a blue dot may be utilized on a separate computing system to represent the location of the user 302 for one or more parties authorized to view the location of the user 302.

The biometric reader 304 may be configured to measure temperature, glucose levels, blood oxygenation, blood pressure, and any number of other characteristics, parameters, or biometrics of the user 302. The biometric reader 304 may also include actuators that indicate the orientation of user 302. For example, the biometric reader 304 may indicate whether the user 302 is standing, sitting, or laying. In one embodiment, if the user 302 is determined to be laying in a position that is not associated with a bed, couch, or so forth, an alert may be generated for an authorized party. In one embodiment, the biometric reader 304 is a smart watch (e.g., Apple watch) that communicates wirelessly with the lockbox 308 through the antenna 312).

Figure 4:
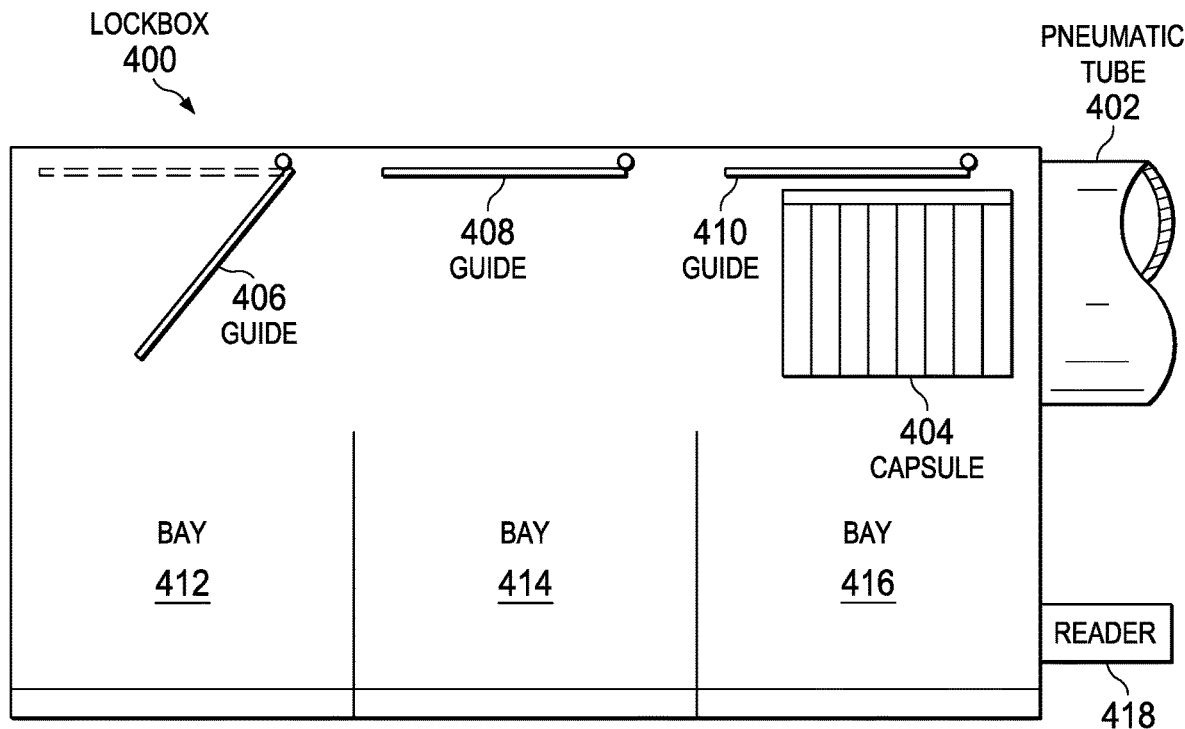
FIG. 4 is a partially cut-away top view of a lockbox 400 in accordance with an illustrative embodiment.

FIG. 4 is a partially cut-away top view of a lockbox 400 in accordance with an illustrative embodiment. The lockbox 400 may be integrated with or connected to a wall, floor, or other structure within a residence. In one embodiment, a pneumatic tube 402 may be part of a pneumatic system as is herein described. The pneumatic tube 402 may be attached to the lockbox 400 utilizing any number of couplings. A container 404 is communicated through the pneumatic tube 402 to the lockbox 400. In one embodiment, the lockbox 400 may include guides 406, 408, 410. In one embodiment, the guides 406, 408, 410 are arms that may rotate about a pivot point, flex, or otherwise move to guide the container 404 to one of the bays 412, 414, 416. For example, as shown in FIG. 4 the guide 406 may pivot to guide the container 404 to the bay 412.

The guides 406, 408, 410 may guide the container 404 into one of multiple bays 412, 414, 416. The guides 406, 408, 410 may also represent magnetic, air pressure, or other mechanical diverting systems. The lockbox 400 may include any number of bays 412, 414, 416 or different containers. For example, the lockbox 400 may include a bay for each day of the week so that medications may be easily separated based on the day of the week for the clarity of the user. In one embodiment, each of the bays 412, 414, 416 may be accessed individually by multiple doors, or collectively, utilizing a larger door. In another embodiment, the lockbox 400 may include a single guide and bay for simple operation.

The reader 418 authenticates the identity of the user. In one embodiment, the reader 418 utilizes an authentication signal, device (e.g., RFID chip, proximity to wireless device or identifier, etc.), biometric read from the user, combination, or other secure identifier. For example, the reader 418 may analyze a voice sample provided by the user, a fingerprint, retinal identification, or other user information.

Figure 5:
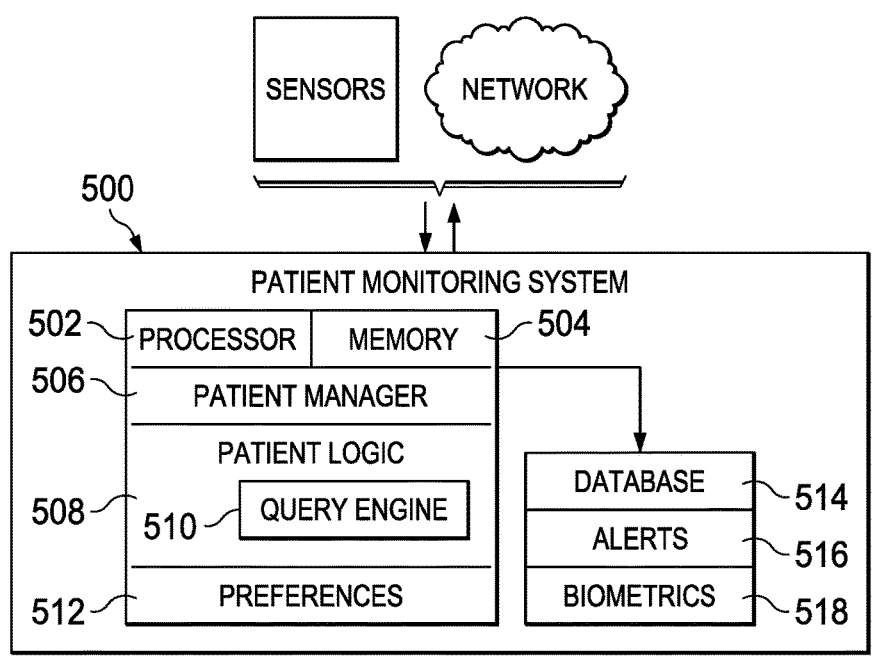
FIG. 5 is a block diagram of a patient monitoring system in accordance with an illustrative embodiment.

FIG. 5 is a block diagram of a patient monitoring system 500 in accordance with an illustrative embodiment. In one embodiment, the patient monitoring system 500 may include a processor 502, a memory 504, a patient manager 506, patient logic 508, a query engine 510, preferences 512, a database 514, alerts 516, and biometrics 518. The patient monitoring system 500 may communicate with a network 520 and sensors 522. The patient monitoring system 500 may be representative of any number of computing or communications devices. Various other components, modules, and units may be included in the patient monitoring system 500 that are not described for purposes of brevity. For example, the patient monitoring system 500 may include any number of processors, memory, chipsets, cards, buses, interfaces, ports, connections, storage systems, and so forth.

The patient monitor 506 is configured to store and manage information for a number of patients. The patient logic 508 may represent digital logic, firmware, software, or a combination thereof, for performing distribution, monitoring, and management of one or more patients. The query engine 510 may be configured to query data within the database 514, as well as other portions of the patient monitoring system 500.

The preferences 512 control parameters, criteria, and user preferences that control how the patient, distribution, monitoring, and management is performed by the systems herein described. For example, how frequently are one or more users contacted to determine their status, when are monitoring systems activated and analyzed, and how are the users monitored and cared for. The database 514 stores information and data for the patients that are associated with the patient monitoring system 500.

The alerts 516 are configured to send alerts to one or more designated parties. For example, a number of different individuals may be notified through software alert, text message, email, phone call, or other types of communication. The conditions for the alerts 516 may be specified by the preferences 512 or the alerts 516.

The biometrics 518 store biometric information for a number of users. The biometric information may be utilized to authenticate the user. The biometrics 518 may also be utilized to determine the status of a user. For example, the biometrics 518 may include thresholds for determining whether the user is within acceptable levels, such as temperature, heart rate, blood pressure, hormone levels, chemical levels and excretions, pupil dilation, response times, and so forth.

Figure 6:
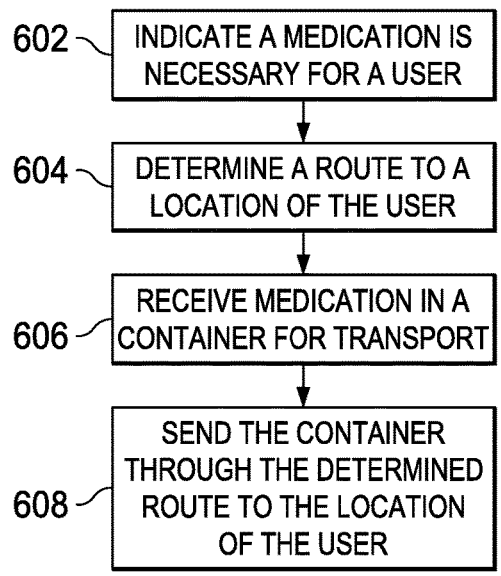
FIG. 6 is a flowchart of a process for delivering medication in accordance with an illustrative embodiment.

FIG. 6 is a flowchart of a process for delivering medication in accordance with an illustrative embodiment. The process of FIG. 6 may be implemented by one or delivery systems or devices. The systems or devices may be stand-alone devices or may be interconnected or networked.

The process of FIG. 6 may begin by indicating medication is necessary for a user (602). In one embodiment, prescriptions or other medications may be tracked by a system that tracks one or more users. Information regarding the medications necessary for the user may be received before delivery or at any time by the user himself/herself, family member or friend, doctor, or other medical professional.

Next, the system determines a route to a location of the user (step 604). The location may be representative of any number of temporary or permanent locations, residences, or so forth of the user. In one embodiment, the route may include commands for the system to route a shuttle or other container including medication through a pneumatic system to the location of the user. For example, a smart shuttle containing medication for a week may be routed to a lockbox in an assisted living facility of the user. In another embodiment, the route may also be driving instructions for a delivery person to drive to the location including, driving instructions, a house number, an apartment number, and so forth. In yet another embodiment, the route may be flying or driving instructions for a drone from a first location to the second location associated with the user. For example, flying instructions may include a flight path and instructions for landing on a pad, connecting to the docking system, authenticating delivery, or so forth.

Next, the system receives medication in a container for transport (step 606). The container represents any number of shuttles, vessels, or devices. For example, the container may include a smart shuttle. The shuttle may include logic for controlling distribution of the medication(s) stored within. In one embodiment, the shuttle may include multiple segments, portions, or chambers for storing medications for meals, days of the week, time periods, or so forth.

Next, the system sends the container through the determined route to the location of the user (step 608). For example, the container may be sent through a delivery system (e.g., pneumatic tubes, air drone, land drone, etc.) or route. The container may be sent to a holding container or lockbox to secure delivery at the location. Any number of alerts, confirmations, or alarms may be played to the user in response to the container being received. Confirmations may also be sent indicating that the container has arrived at the selected destination.

Figure 7:
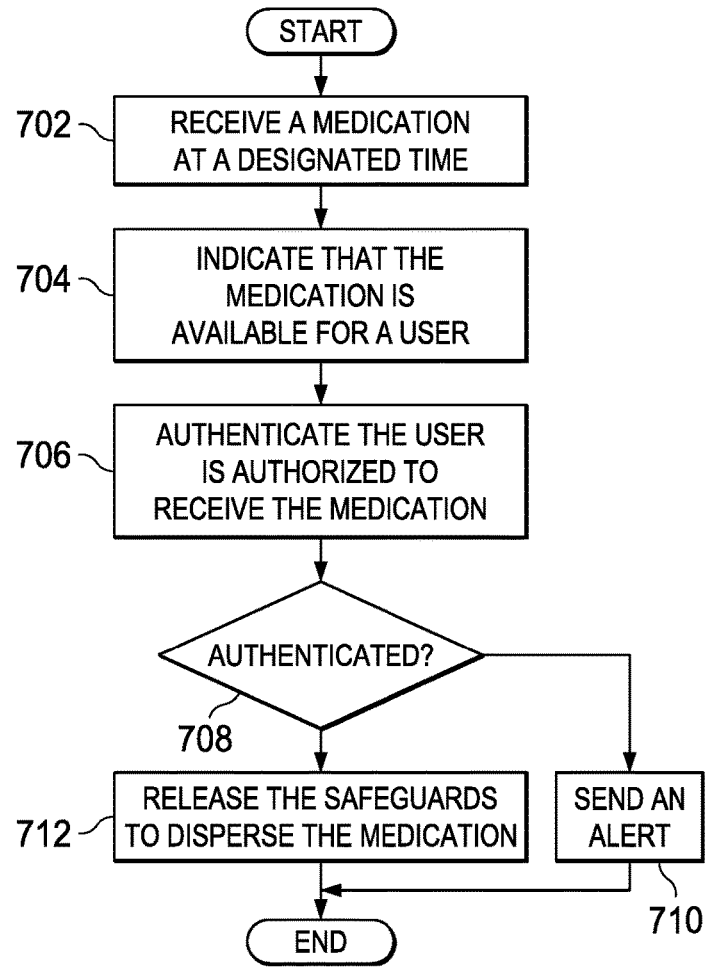
FIG. 7 is a flowchart of a process for dispensing medication in accordance with an illustrative embodiment.

FIG. 7 is a flowchart of a process for dispensing medication in accordance with an illustrative embodiment. In one embodiment, the process of FIG. 7 may begin by receiving a medication at a designated time (step 702). As previously noted, the medication may be received through any number of delivery systems, mechanisms, or devices. In one embodiment, the medication may be communicated as needed (e.g., in real-time). In another embodiment, the medication may be delivered by day, time period, meal, or so forth. The medication may be delivered or made available by a lockbox or a shuttle temporarily storing the medication.

Next, the system indicates that the medication is available for a user (step 704). Any number of alerts, indicators, information, or messages may be communicated to the user during step 704. The indications provided by the system may be communicated audibly, visually, tactilely, or utilizing a combination of sensory systems. In one embodiment, a custom message pre-recorded by the user (or a family member, friend, doctor, or associated medical professional) may be played to the user. For example, the adult child of a user may provide instructions for the user (an elderly parent) to take medicine with lunch. The indications provided during step 704 may also be communicated to external systems or devices, such as monitoring systems, mobile devices, televisions, media devices, or so forth. The indication may be given once the medication is received or at the time the medication is to be taken by the user.

Next, the system authenticates the user is authorized to receive the medication (step 706). Authentication may be performed utilizing any number of methodologies. In various illustrative embodiments, the user may be prompted to provide one or more biometrics, pin numbers, passwords, identifiers, or so forth. The authentication may also be performed based on a tag, chip, or other identifying device associated with the user. For example, the user may be prompted to provide a voice authentication and fingerprint in order to authorize the release or complete delivery of the medication. In one embodiment, authentication of the user may be performed by a third party. For example, a video camera may be utilized to authenticate that the user is the party retrieving the information and not an unauthorized party.

Next, the system determines whether the user is authenticated (step 708). The system may provide the user a preset number of times to perform the authentication in step 706. As a result, the user is not automatically prevented from receiving the medicine in response to incorrect memory or momentary lapses. If the user is not authenticated during step 708, the system sends an alert (step 710). The alert may be sent to any number of designated parties including, but not limited to, the user, administrator, a doctor, a caregiver, family members, friends, medical professionals, or so forth. The alert 710 may specify why the authentication failed, what types of medications were being retrieved, and other information. The alert provides for additional security and may be utilized to deter unauthorized access or inappropriate use of the system.

In response to determining that the user is authenticated during step 708, the system releases safeguards to dispense the medication (step 712). The safeguards may include one or more lock, or securing mechanisms that may secure the medication. For example, the associated lockbox, shuttle chamber, or so forth, may be opened delivering the medication to the user. During step 712, the system may also provide instructions to the user for taking the medication. For example, the instructions may include information regarding whether the medication is to be ingested (time period), applied to the skin or other tissue, taken as part of a meal, taken with water, or other applicable information. In one embodiment, a camera or tracking system integrated within the lockbox or residence may be utilized to ensure that the medications are taken properly.

Figure 8:
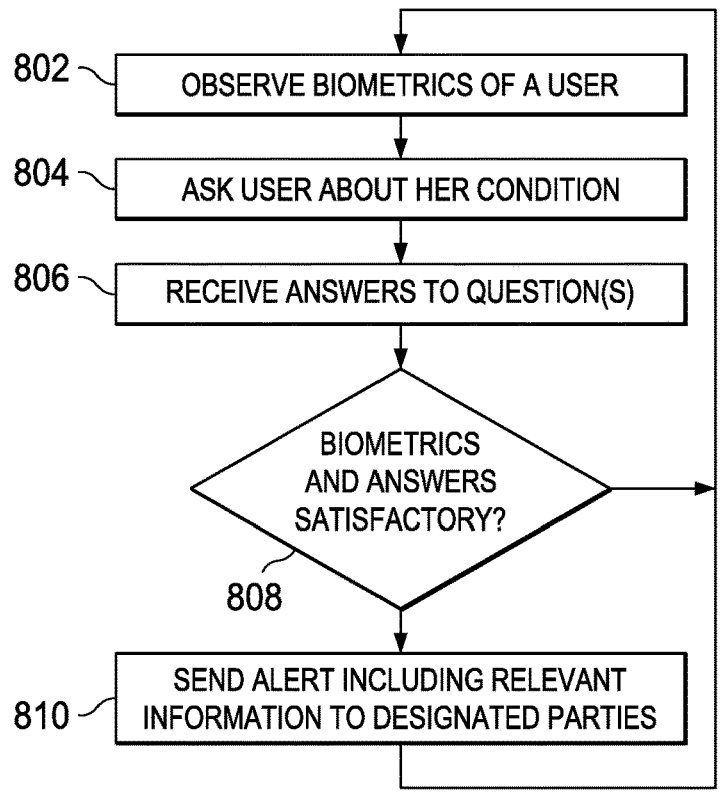
FIG. 8 is a flowchart of a process for monitoring a user in accordance with an illustrative embodiment.

FIG. 8 is a flowchart of a process for monitoring a user in accordance with an illustrative embodiment. The process of FIG. 8 may be implemented by a monitoring system. The process may begin by observing biometrics of a user (step 802). The user may represent a resident of a facility, patient, or other similar individual. The biometrics may include heart rate, pupil dilation, temperature, movements, facial expressions, blood analysis, breathing, odor, hormone levels, chemical excretions, position within an area (e.g., sitting, prone, kneeling, etc.), and so forth.

Next, the system asks the user about her condition (step 804). In one embodiment, the questions asked of the user may be played through one or more speakers, televisions, or so forth associated with the location of the user. The questions may be posed audibly, textually, electronically, or utilizing any number of other methods utilized by the user for communications (e.g., braille). The questions may also be posed utilizing a mobile device associated with the user, such as a smart phone or watch. The questions posed to the user may be preprogrammed by a medical professional, such as a doctor of the user. The questions may have any number of conditions, including time of day, biometric association, position, or so forth. For example, if the user is lying down in a position that is not associated with a couch or bed, the system may automatically ask the user if she is okay. In another example, a question may be posed in response to an elevated or low heart rate of the user to ensure that a medical event is not occurring. In yet another example, a number of questions may be posed throughout the day during specified time periods, such as meals, to check the status and well-being of the user. As is subsequently described, negative response or non-responses may be reported to one or more caregivers, administrators, family members, or other designated parties.

Next, the system receive answers to the questions (step 806). The answers relate to the questions posed during step 804. The answers may be received through one or more microphones directly or indirectly communicating with the system. For example, microphones within a bedroom may receive the answers. Alternatively, the microphone of a mobile device worn or carried by the user may be configured to receive answers and other input from the user. The answer may also be the lack of a response or a non-response that may be indicative of a potential problem. For example, the question may be posed utilizing a different system, such as an audio question instead of just a visual question presented on a wireless device or television.

Next, the system determines whether the biometrics and answers received are satisfactory (step 808). Determinations of whether the biometrics and answers are satisfactory may be determined utilizing a database, conditions, factors, or other information associated with the user or her response. For example, thresholds, or levels may be utilized to determine whether a biometric is exceeded. The answers may be analyzed to determine response time (e.g., delay in responding), speech pattern, speech cadence, words utilized during the response, and so forth. In one embodiment, the biometrics and answers throughout the day, week, and year may be archived for subsequent reference. For example, the biometric information may be utilized to determine improvements in behavior, treatment plans, condition, or so forth for the user. In another embodiment, the biometric information may be sent to a user for a decision by an administrator, medical professional, or so forth. The question and response may be sent to determine the real-time condition of the user.

If the system determines that the biometrics and answers are satisfactory during step 808, the system returns to observe biometrics of the user (step 802). If the system determines that the biometrics and answers are not satisfactory during step 808, the system sends an alert including relevant information to designated parties (step 810). The alert may be any number of messages, indicators, or other information. For example, the alert may include the biometrics, the response provided by the user, video recordings, user biometrics, audio recordings, or so forth. The designated parties may include administrators, caregivers, family, friends, or other parties designated to receive information regarding the user. As a result, the designated parties may be kept informed of the status or condition of the user even if remote from the location of the user.

Embodiments may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments of the inventive subject matter may take the form of a computer program product embodied in any tangible medium of expression having computer usable program code embodied in the medium. The described embodiments may be provided as a computer program product, or software, that may include a machine-readable medium having stored thereon instructions, which may be used to program a computer system (or other electronic device(s)) to perform a process according to embodiments, whether presently described or not, since every conceivable variation is not enumerated herein. A machine readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read only memory (ROM); random access memory (RAM); erasable programmable memory (e.g., EPROM and EEPROM); flash memory; or other types of medium suitable for storing electronic instructions. In addition, embodiments may be embodied in an electrical, optical, acoustical or other form of propagated signal (e.g., carrier waves, infrared signals, digital signals, etc.), or wireline, wireless, or other communications medium.

Computer program code for carrying out operations of the embodiments may be written in any combination of one or more programming languages, including an object oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a personal area network (PAN), or a wide area network (WAN), or the connection may be made to an external computer (for example, through the Internet using an Internet Service Provider).

Turning again to FIG. 1, in one embodiment, the computing system 118 may include a processor unit (not shown, possibly including multiple processors, multiple cores, multiple nodes, and/or implementing multi-threading, etc.). The computer system 188 includes memory. The memory may be system memory (e.g., one or more of cache, SRAM, DRAM, zero capacitor RAM, Twin Transistor RAM, eDRAM, EDO RAM, DDR RAM, EEPROM, NRAM, RRAM, SONOS, PRAM, etc.) or any one or more of the above already described possible realizations of machine-readable media. The computer system 188 also includes a bus (e.g., PCI, ISA, PCI-Express, HyperTransport®, InfiniBand®, NuBus, etc.), a network interface (e.g., an ATM interface, an Ethernet interface, a Frame Relay interface, SONET interface, wireless interface, etc.), and a storage device(s) (e.g., optical storage, magnetic storage, etc.). The system memory embodies functionality to implement embodiments described above. The system memory may include one or more functionalities that facilitate tracking a user, managing medication deliveries and consumption, and the other illustrative embodiments. Any one of these functionalities may be partially (or entirely) implemented in hardware and/or on the processing unit. For example, the functionality may be implemented with an application specific integrated circuit, in logic implemented in the processing unit, in a co-processor on a peripheral device or card, etc. Further, realizations may include fewer or additional components not illustrated in FIG. 1 (e.g., video cards, audio cards, additional network interfaces, peripheral devices, etc.). The processor unit, the storage device(s), and the network interface are coupled to the bus YY03. Although illustrated as being coupled to the bus, the memory may be coupled to the processor unit.

While the embodiments are described with reference to various implementations and exploitations, it will be understood that these embodiments are illustrative and that the scope of the inventive subject matter is not limited to them. In general, techniques for tracking, monitoring, and delivering medication to a user in as described herein may be implemented with facilities consistent with any hardware system or hardware systems. Many variations, modifications, additions, and improvements are possible.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the inventive subject matter. In general, structures and functionality presented as separate components in the exemplary configurations may be implemented as a combined structure or component. Similarly, structures and functionality presented as a single component may be implemented as separate components. These and other variations, modifications, additions, and improvements may fall within the scope of the inventive subject matter.

What is claimed is:

1. A method for medication delivery comprising:
   receiving information indicating a user is scheduled to receive a medication at a residence of the user, a scheduled delivery of the medication is enabled to be associated with a predetermined schedule, real-time delivery, and based on a request from a user;
   determining a route between a dispensary storing a plurality of medications including the medication and the residence of the user utilizing a drone;
   sending the medication in a container from the dispensary to the residence of the user utilizing the route navigated by the drone;
   docking the drone with a lockbox at the residence and securely delivering the container to the lockbox during docking thereby securing the medication;
   notifying the user that the medication has been received at the residence based on delivery by the drone for consumption utilizing one or more systems integrated with the residence;
   authenticating the user is authorized to receive and take the medication utilizing at least one or more biometrics;
   releasing safeguards of the lockbox to dispense the medication at the residence of the user from the container after delivery by the drone for utilization by the user in response to receiving the one or more biometrics at least one of which identifies the user through the one or more systems integrated with the residence of the user and separate from the container; and
   providing instructions for the user to take the medication received at the lockbox through the one or more systems integrated with the residence in response to releasing the safeguards.

2. The method of claim 1, further comprising:
   receiving the medication in the container, wherein the container is configured for transport by the drone.

3. The method of claim 1, wherein the drone navigates airspace between at least the dispensary and the residence of the user avoiding permanent and temporary obstacles.

4. The method of claim 1, wherein the one or more systems integrated at the residence include at least biometric sensors, speakers, and visual indicators.

5. The method of claim 4, wherein the speakers provide the instructions for the user to take the medication.

6. The method of claim 1, wherein the medication is sent in real-time in response to a medical reading of the user read by the biometric wearable exceeding a threshold.

7. The method of claim 1, further comprising:
   authenticating the user utilizing the one or more biometrics in response to the container being delivered to the residence of the user; and
   releasing the medication to the user to be taken in response to authenticating the user utilizing the one or more biometrics and a condition of the user.

8. The method of claim 7, wherein the authenticating is performed utilizing a biometric identifier associated with the user, wherein the container is configured for transport by the drone.

9. The method of claim 1, wherein the container includes a plurality of compartments associated with medications for different times.

10. The method of claim 1, wherein the medication is sent automatically through the drone to the residence in response to the one or more medical readings of the user read by a biometric wearable at the residence being communicated to the dispensary, wherein the medication is automatically sent a plurality of times throughout a day based on at least a schedule or the biometric reading ready by the biometric wearable.

11. A system for delivering medication, the system comprising:
   a drone delivery system including at least a drone capable of navigating between one or more residences and a dispensary storing a plurality of medications;
   a lockbox at the one or more residences configured to dock with the drone to securely receive a medication from the plurality of medications when the drone is docked with the lockbox; and
   a computing system to receive information indicating a user is scheduled to receive a medication at the one or more residences associated with the user, determine a route for the drone between the dispensary and the one or more residences associated with the user, send the medication in a container from the dispensary to the one or more residences associated with the user utilizing the route navigated by a drone, notify the user that the medication has been received at the lockbox at the one or more residences associated with the user as delivered by the drone utilizing one or more systems integrated at a location of the one or more residences, authenticate the user is authorized to receive and take the medication utilizing at least one or more biometrics, wherein the lockbox receives the container from the drone and secures the medication until authorized for release by the user, release the safeguards of the lockbox at the one or more residences associated with the user to dispense medication from the container for utilization by the user in response to receiving the one or more biometrics from the user through the one or more systems integrated at the location and separate from the container, and provide instructions for the user to take the medication received at the residence through the one or more systems in response to releasing the safeguards of the lockbox at the one or more residences, wherein the container requires one of the one or more biometrics identify the user to be read from a biometric wearable to release the medication, and wherein the medication is enabled to be delivered according to a predetermined schedule, real-time delivery, and based on a request from the user.

12. The system of claim 11, wherein the one or more systems integrated at the location include at least speakers and visual indicators.

13. The system of claim 12, wherein the lockbox integrated with the one or more residences releases the medication to the user in response to the user providing an identifier and the one or more biometrics.

14. The system of claim 12, wherein the container includes a plurality of compartments associated with medications for different times.

15. The system of claim 12, wherein the computing system prompts the user to take the medication in the one or more residences associated with the user and provides instructions for the user to take the medication.

16. The system of claim 11, further comprising: lockboxes at each of the one or more residences including the lockbox for receiving the container and securing the medication until authorized for release by the user.

17. The system of claim 11, wherein the medication is sent automatically through the drone to the residence in response to a medical reading of the user read by the biometric wearable at the residence being communicated to the dispensary.

18. A system for delivering medication, comprising:
a server storing instructions in a memory therein, and one or more processors that execute the instructions to:
receive information indicating a user is scheduled to receive medication, a scheduled delivery of the medication is enabled to be associated with a predetermined schedule, a real-time delivery, and based on request from the user;
determine a route between a dispensary and a residence of the user utilizing a drone;
send the medication in a container from the dispensary to the residence of the user utilizing the route navigated by the drone, wherein the drone docks with a lockbox so that the container is received by the lockbox;
dock the drone with a lockbox at the residence and securely delivering the container to the lockbox for securing the medication;
notify the user that the medication has been received at a lockbox of the residence for consumption utilizing one or more systems integrated at the location;
authenticate the user is authorized to receive and take the medication received at the lockbox of the residence utilizing at least one or more biometrics;
release the safeguards of the lockbox at the residence of the user to dispense medication from the container for utilization by the user in response to receiving one or more biometrics at least one of which identifies the user through the one or more systems integrated with the residence, wherein the container requires the at least one of the one or more biometrics which identifies the user to be read from a biometric wearable to release the medication;
provide instructions for the user to take the medication received at the residence in response to releasing the safeguards; and
a drone delivery system including at least the drone capable of navigating between the dispensary and the residence of the user for delivering the medication in the container to the lockbox.

19. The system of claim 18, wherein the instructions are further executed to:
indicate to the user that the medication is available to be taken and provide the instructions for taking the medication.

20. The system of claim 18, wherein the instructions are further executed to:
authenticate the user utilizing the one or more biometrics in response to the container being delivered to the lockbox at the residence of the use by the drone, wherein the user at least temporarily resides at the location; and
release the medication to the user to be taken in response to authenticating the user utilizing the one or more biometrics and determining a condition of the user.

* * * * *